United States Patent [19]

Vallee et al.

[11] Patent Number: 5,286,487
[45] Date of Patent: Feb. 15, 1994

[54] COVALENT ANGIOGENIN/RNASE HYBRIDS

[75] Inventors: Bert L. Vallee, Brookline; Michael D. Bond, Brighton, both of Mass.

[73] Assignee: President and Fellows of Harvard College, Cambridge, Mass.

[21] Appl. No.: 953,555

[22] Filed: Sep. 29, 1992

Related U.S. Application Data

[63] Continuation of Ser. No. 481,342, Feb. 15, 1990, abandoned.

[51] Int. Cl.$^5$ .................. A61K 37/54; C12N 9/22; C12N 15/00
[52] U.S. Cl. .................. 424/94.6; 435/199; 514/2; 935/10; 935/14
[58] Field of Search .................. 435/199, 172.1, 172.3; 935/10, 14; 514/2.12; 424/94.6

[56] References Cited

U.S. PATENT DOCUMENTS

| | | | |
|---|---|---|---|
| 4,229,531 | 10/1980 | Tolbert et al. | 435/41 |
| 4,503,038 | 3/1985 | Banda et al. | 424/95 |
| 4,721,672 | 1/1988 | Vallee et al. | 435/70 |
| 4,727,137 | 2/1988 | Vallee et al. | 530/412 |

FOREIGN PATENT DOCUMENTS

| | | |
|---|---|---|
| 0292763A2 | 7/1988 | European Pat. Off. |
| 3716722 | 5/1987 | Fed. Rep. of Germany |

OTHER PUBLICATIONS

Harper, et al., "Enzymatically Active Angiogen/Ribonuclease A Hybrids . . . ", *Biochemistry*, vol. 27, No. 1, 1988, pp. 219-226.
Kurachi, et al., "Sequence of the cDNA and Gene for Angiogenin . . . ", *Biochemistry*, vol. 24, No. 20, 1985, pp. 5494-5499.
Greenblatt and Shubik, 1968, J. Natl. Cancer Inst. 41: 111-124.
Auerbach, *Lymphokines*, Pick and Landy, eds. 69-88, Academic Press, New York, 1981.
Berman et al., 1982, Invest. Ophthalmol. Vis. Sci. 22: 191-199.
Raju et al., 1982, J. Natl. Cancer Inst. 69: 1183-1188.
Banda et al., 1982, Proc. Natl. Acad. Sci. USA 79: 7773-7777.
D'Amore et al., 1981, Proc. Natl. Acad. Sci. USA 78: 3068-3072.
Folkman et al., 1971, J. Exp. Med. 133: 275-288.
Tuan et al., 1973, Biochemistry 12: 3159-3165.
Phillips and Kumar, 1979, Int. J. Cancer 23: 82-88.
Weiss et al., 1979, Br. J. Cancer 40: 493-496.
Fenselau et al., 1981, J. Biol. Chem. 256: 9605-9611.
Kumar et al., 1983, Int. J. Cancer 32: 461-464.
Vallee et al., 1985, Experientia 41: 1-15.

(List continued on next page.)

*Primary Examiner*—Robert A. Wax
*Assistant Examiner*—Keith D. Hendricks
*Attorney, Agent, or Firm*—Allegretti & Witcoff, Ltd.

[57] ABSTRACT

Regional mutagenesis of a gene for angiogenin to produce DNA sequences encoding mutant proteins having increased angiogenic activity are disclosed. Expression vectors containing these sequences are introduced into host cells and direct the production of mutant angiogenic proteins with markedly increased angiogenic activity. Replacement of amino acids in a region at or corresponding to residues 8-22 of angiogenin, with other amino acids, in particular, with amino acids corresponding to residues 7-21 of RNase, unexpectedly yields a mutant angiogenin/RNase hybrid protein with 10-fold increased angiogenic potency in the chorioallantoic membrane assay. Other in vivo and in vitro angiogenin-related activities are altered in the mutant hybrid protein. Mutant angiogenin/RNase hybrid proteins according to the present invention are useful therapeutic compositions to promote the development of a hemovascular network in a mammal or to promote wound healing, in particular, healing of torn or traumatized fibrocartilage material.

8 Claims, 9 Drawing Sheets

OTHER PUBLICATIONS

Fett et al., 1985, Biochemistry 24: 5480-5486.
Shapiro et al., 1986, Biochemistry 25: 3527-3532.
Denefle et al., 1987, Gene 56: 61-70.
Strydom et al., 1985, Biochemistry 24: 5486-5494.
Knighton et al., 1977, Br. J. Cancer 35: 347-356.
Langer and Folkman, 1976, Nature 263: 797-800.
Shapiro et al., 1987, Proc. Natl. Acad. Sci. USA 84: 8783-8787.
McCarthy et al., 1985, The EMBO Journal 4: 519-526.
McCarthy et al., 1986, Gene 41: 201-206.
Shapiro et al., 1987, Biochemistry 26: 5141-5146.
Blackburn, 1979, J. Biol. Chem. 254: 12484-12487.
Shapiro and Vallee, 1987, Proc. Natl. Acad. Sci. USA 84: 2238-2241.
St. Clair et al., 1987, Proc. Natl. Acad. Sci. USA 84: 8330-8334.
Bicknell and Vallee, 1988, Proc. Natl. Acad. Sci. USA 85: 5961-5965.
Bicknell and Vallee, 1989, Proc. Natl. Acad. Sci. USA 86: 1573-1577.
St. Clair et al., 1988, Biochemistry 27: 7263-7268.
Lee et al., 1989b, Biochemistry 28: 225-230.
Palmer et al., 1986, Proc. Natl. Acad. Sci. USA 83: 1965-1969.
Shapiro et al., 1988, Anal. Biochem. 175: 450-461.
Shapiro et al., 1988, Biochem. Biophys. Res. Commun. 156: 530-536.
Shapiro et al., 1989, Biochemistry 28: 1726-1732.
Shapiro and Vallee, 1989, Biochemistry 28: 7401-7408.
Hofmann et al., 1966, J. Amer. Chem. Soc. 88: 3633-3639.
Lee et al., 1989, Biochemistry 28: 219-224.
Lee and Vallee, 1989, Biochemistry 28: 3556-3561.
Lee et al., 1989, Biochem. Biophys. Res. Commun. 161: 121-126.
Blackburn and Jailkhani, 1979, J. Biol. Chem. 254: 12488-12493.
Maes et al., 1988, FEBS Lett. 241: 41-45.
Bond and Strydom, 1989, Biochemistry 28: 6110-6113.
Kurachi et al., 1988, Biochemistry 27: 6557-6562.

a

```
                    1              *  *  *                  *  *
RNase A             KETAAAKFERQHMDSSTSAASSSNYC...
                                 10           20
                *  *      *  *  *  *
Angiogenin   <QDNSRYTHFLTQHYDAKPQGRDDR--YC...
                              10           20
ARH-III      <QDNSRYTKFERQHMDSSTSAASDR--YC...
                              10           20
``` b

```
       S     R     Y     T     K     F     E     R     Q     H
5' [TCG   AGG   TAT   ACA   AAA   TTC   GAA   CGC   CAG   CAC
3'  ]CC   ATA   TGT   TTT   AAG   CTT   GCG   GTC   GTG

M     D     S     S     T     S     A     A     S     D
    ATG   GAC   TCT   TCG   ACA   AGC   GCT   GCC   TCC   GAT] 3'
    TAC   CTG   AGA   AGC   TGT   TCG   CGA   CGG   AGG   C[  5'
```

FIG. 2

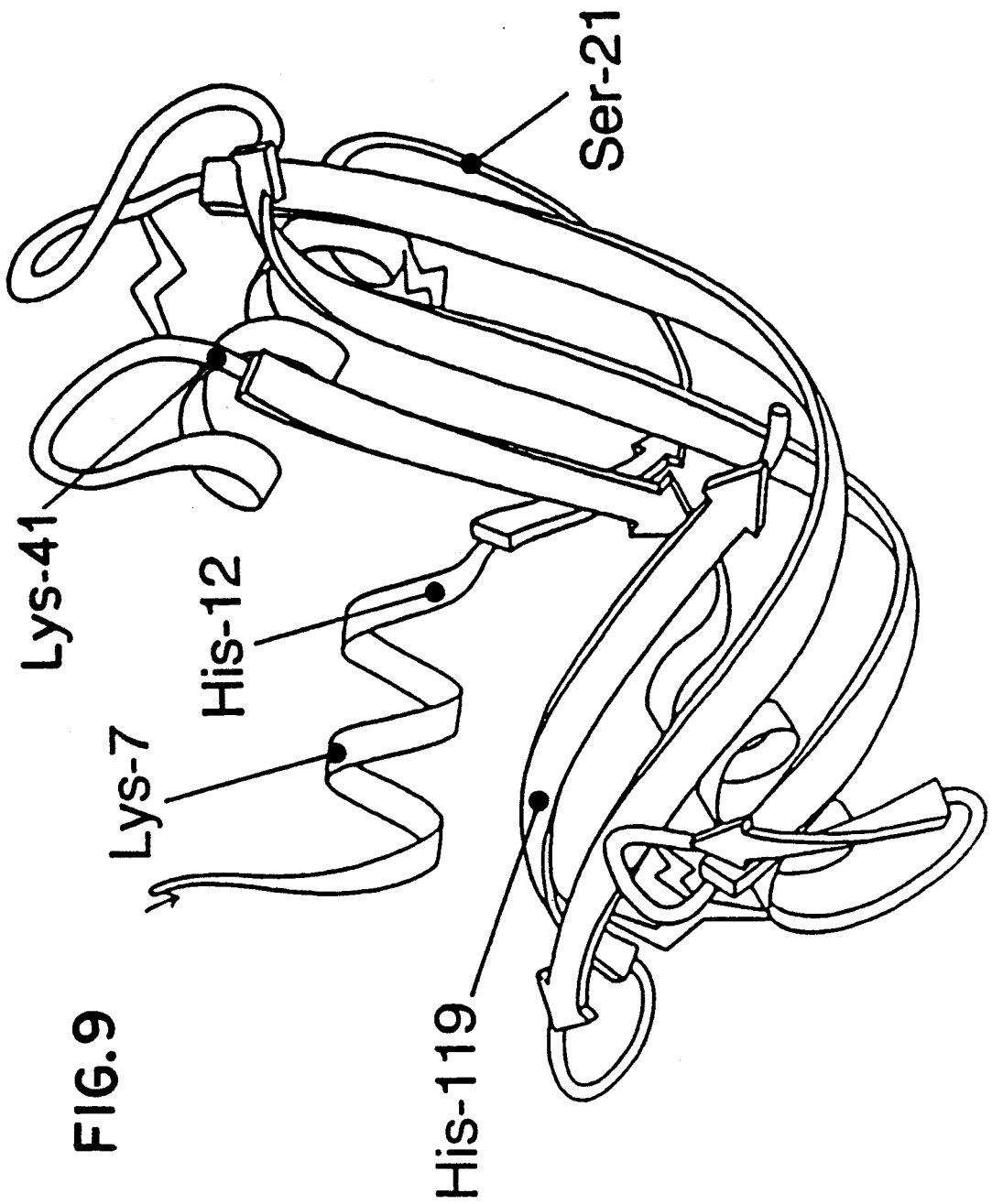

COVALENT ANGIOGENIN/RNASE HYBRIDS

This application is a continuation of application Ser. No. 07/481,342 filed Feb. 15, 1990, now abandoned.

BACKGROUND OF THE INVENTION

1. Field of the Invention

This invention relates to modified or mutant angiogenin proteins and DNA sequences which encode the modified or mutant proteins. Additionally, the invention relates to vectors, host cells and methods of expression of the modified or mutant angiogenin proteins. In particular, the modified or mutant angiogenin proteins of the present invention are genetically engineered covalent angiogenin/ribonuclease (RNase) hybrids. These hybrids are useful for the identification of structural components of angiogenin necessary for angiogenin's characteristic activities. In particular, regional mutagenesis may be used to generate such angiogenin/RNase hybrid proteins, which are derivatives of angiogenin in which particular regions of primary structure have been replaced with the corresponding segments of RNase. Preparation and characterization of such proteins allows the identification of segments, such as an N-terminal segment according to the present invention, that may be critical to angiogenin's characteristic activities. Specifically, the present invention relates to a novel recombinant hybrid protein with increased angiogenic potency, ARH-III, in which N-terminal residues 8-22 of angiogenin are replaced by the corresponding region (residues 7-21) of RNase via regional mutagenesis. Such recombinant mutant angiogenin proteins may be produced in sufficient quantities to permit their application as therapeutics or diagnostics.

2. Background of the Art

Angiogenesis, the process of developing a hemovascular network, is essential for the growth of solid tumors and is a component of normal wound healing and growth processes. It has also been implicated in the pathophysiology of atherogenesis, arthritis, and diabetic retinopathy. It is characterized by the directed growth of new capillaries toward a specific stimulus. This growth, mediated by the migration of endothelial cells, may proceed independently of endothelial cell mitosis.

The molecular messengers responsible for the process of angiogenesis have long been sought. Greenblatt and Shubik, 1968, J. Natl. Cancer Inst. 41: 111-124, concluded that tumor-induced neovascularization is mediated by a diffusible substance. Subsequently, a variety of soluble mediators have been implicated in the induction of neovascularization. These include prostaglandins (Auerbach, in *Lymphokines*, Pick and Landy, eds., 69-88, Academic Press, New York, 1981), human urokinase (Berman et al., 1982, Invest. Opthalm. Vis. Sci. 22: 191-199), copper (Raju et al., 1982, J. Natl. Cancer Inst. 69: 1183-1188), and various "angiogenesis factors."

A variety of angiogenesis factors have been derived from tumor cells, wound fluid (Banda et al., 1982, Proc. Natl. Acad. Sci. USA 79: 7773-7777; Banda et al., U.S. Pat. No. 4,503,038), and retinal cells (D'Amore, 1981, Proc. Natl. Acad. Sci. USA 78: 3068-3072). Tumor-derived angiogenesis factors have in general been poorly characterized. Folkman et al., 1971, J. Exp. Med. 133: 275-288, isolated tumor angiogenesis factor from the Walker 256 rat ascites tumor. The factor was mitogenic for capillary endothelial cells and was inactivated by RNase. Tuan et al., 1973, Biochemistry 12: 3159-3165, found mitogenic and angiogenic activity in the nonhistone proteins of the Walker 256 tumor. The active fraction was a mixture of proteins and carbohydrate. A variety of animal and human tumors have been shown to produce angiogenesis factor(s) (Phillips and Kumar, 1979, Int. J. Cancer 23: 82-88, but the chemical nature of the factor(s) was not determined. A low molecular weight non-protein component from Walker 256 tumors has also been shown to be angiogenic and mitogenic (Weiss et al., 1979, Br. J. Cancer 40: 493-496). An angiogenesis factor with a molecular weight of 400-800 daltons was purified to homogeneity by Fenselau et al., 1981, J. Biol. Chem. 256: 9605-9611, but it was not further characterized. Human lung tumor cells have been shown to secrete an angiogenesis factor comprising a high molecular weight carrier and a low molecular weight, possibly non-protein, active component (Kumar et al., 1983, Int. J. Cancer 32: 461-464). Vallee et al., 1985, Experientia 41: 1-15, found angiogenic activity associated with three fractions from Walker 256 tumors. Tolbert et al. (U.S. Pat. No. 4,229,531) disclose the production of angiogenesis factor from the human adenocarcinoma cell line HT-29, but the material was only partially purified and was not chemically characterized. Isolation of genes responsible for the production of the above described angiogenesis factors has not been reported at least in part due to the lack of purity and characterization of the factors.

Isolation of angiogenesis factors has employed a number of different techniques, including: high performance liquid chromatography (Banda et al., supra); solvent extraction (Folkman et al., supra); chromatography on silica gel (Fenselau et al., supra); DEAE cellulose (Weiss et al., supra), or Sephadex (Tuan et al, supra); and affinity chromatography (Weiss et al., supra).

Vallee et al. (U.S. Pat. No. 4,727,137, which is hereby incorporated by reference) have purified an angiogenic protein from a human adenocarcinoma cell line. This protein has been identified in normal human plasma (Shapiro, et al., 1987, Biochem. 26: 5141-5146). The purified protein, known as angiogenin, was chemically characterized and its amino acid sequence determined. Two distinct activities have been demonstrated for the human tumor-derived angiogenin. First, it was reported to behave as a very potent angiogenic factor in vivo (Fett et al., 1985, Biochem. 24: 5480-5486). Second, it has been found to exhibit a characteristic ribonucleolytic activity toward 28S and 18S rRNA that differs significantly from that of pancreatic RNase in two respects: (a) it requires up to $10^5$ as much angiogenin to obtain the same degree of rRNA degradation as with RNase; and (b) the products are much larger, i.e., from 100 to 500 nucleotides; in addition, it is essentially inactive toward classic RNase A substrates. (Shapiro et al., 1986, Biochem. 25: 3527-3532; St. Clair et al., 1987, Proc. Natl. Acad. Sci. USA 84: 8330-8334).

In addition, Vallee et al. (U.S. Pat. No. 4,721,672, which is also hereby incorporated by reference) have cloned the gene (both cDNA and genomic) encoding the angiogenic protein claimed in U.S. Pat. No. 4,727,137 from a human liver cDNA library and a human genomic library. The angiogenin gene was cloned into vectors and the recombinant vectors encoding the angiogenin gene were used to transform or transfect host cells. Such transformed or transfected cells express a human angiogenin protein.

Based on the sequence of the angiogenin gene described and claimed in U.S. Pat. No. 4,721,672, several groups have prepared synthetic angiogenin genes. Denefle et al., 1987, Gene 56: 61-70, prepared a synthetic gene coding for human angiogenin, which was designed to use codons found in highly expressed *E. coli* proteins. The synthetic gene was ligated into a pBR322-derived expression vector constructed to contain the *E. coli* tryptophan (trp) promoter. This *E. coli*-produced angiogenin was found to be insoluble but could be easily renatured and purified. The purified angiogenin exhibited angiogenic activity and ribonucleolytic activity similar to that described for natural angiogenin purified by Vallee et al. (U.S. Pat. No. 4,727,137) from human adenocarcinoma cells. A different synthetic gene for angiogenin was prepared by Hoechst (German Patent Application P3716722.7) encoding a leucine at amino acid position 30 instead of methionine as found in the natural (i.e. wildtype) angiogenin gene described and claimed in U.S. Pat. No. 4,721,672. This synthetic Leu-30 angiogenin gene was designed to use codons preferentially expressed in *E. coli*. The gene was subcloned into a vector containing a modified trp promoter (European Patent Application 0198415) and a translation initiation region (TIR) sequence (Gene 41: 201-206, 1986; EMBO J. 4: 519-526, 1985) to increase translation efficiency. The synthetic gene is thus under direct control of the trp promoter and expression is induced by addition of indole-3-acrylic acid or by tryptophan starvation. The Leu-30 angiogenin protein could be purified and was found to exhibit angiogenic and ribonucleolytic activity similar to that of the wildtype (Met-30) angiogenin.

All the human angiogenin proteins just described, whether plasma-derived, tumor cell-derived or recombinant DNA-derived (cDNA, genomic DNA or synthetic DNA) exhibit both angiogenic activity and ribonucleolytic activity. Indeed, one of the most intriguing features of angiogenin is its structural homology with mammalian pancreatic RNases. This structural relationship should permit the study of the mechanism of action of angiogenin, as well as the relationship between the angiogenic and enzymatic (i.e. ribonucleolytic) activities of angiogenin.

In vivo, angiogenin is a potent inducer of blood vessel growth as measured by the chick chorioallantoic membrane (CAM) and rabbit cornea assays (Fett et al., 1985, Biochemistry 24: 5480-5486). In vitro, angiogenin induces multiple responses in endothelial cells including activation of phospholipase C and secretion of prostacyclins (Bicknell & Vallee, 1988, Proc. Natl. Acad. Sci. USA 85: 5961-5965; Bicknell & Vallee, 1989, Proc. Natl. Acad. Sci. USA 86: 1573-1577); it also inhibits cell free protein translation by specific cleavage of 18S RNA within the 40S ribosomal subunit (St. Clair et al., 1987, Proc. Natl. Acad. Sci. USA 84: 8330-8334; St. Clair et al., 1988, Biochemistry 27: 7263-7268).

Angiogenin is structurally homologous to the pancreatic RNase family of enzymes, having 34% sequence identity to the most extensively studied member of this group, bovine pancreatic RNase A (RNase A) (Strydom et al., 1985, Biochemistry 24: 5486-5494; Kurachi et al., 1985, Biochemistry 24: 5494-5499). Angiogenin's tertiary structure is similar to that of RNase A as well, based on (i) conservation of three of four disulfide bonds, (ii) extremely tight binding to placental ribonuclease inhibitor (PRI) (Shapiro & Vallee, 1987, Proc. Natl. Acad. Sci. USA 84: 2238-2241; Lee et al., 1989b, Biochemistry 28: 225-230; Blackburn et al., 1977, J. Biol. Chem 252: 5904-5910), and (iii) a computer-generated three-dimensional structure (Palmer et al., 1986, Proc. Natl. Acad. Sci. USA 83: 1965-1969). The three essential catalytic residues of RNase A (His-12, Lys-41, and His-119) are conserved in angiogenin (His-13, Lys-40, and His-114) as are many other key active site and structural residues. Indeed, as stated above, angiogenin does possess ribonucleolytic activity, but of a type far different from other RNases. Angiogenin's activities toward most conventional substrates are five to six orders of magnitude below those of RNase A (Shapiro et al., 1987, Proc. Natl. Acad. Sci. USA 84: 8783-8787; Shapiro et al., 1988, Anal. Biochem. 175: 450-461; Harper & Vallee, 1989, Biochemistry 28: 1875-84). Thus, despite the structural similarities, the vast differences in in vivo and in vitro activities of angiogenin compared to the RNases (which have not been shown to induce angiogenesis or second messenger activities) are clearly indicative of a distinct physiological function for angiogenin.

Recent studies have shown that the active-site histidine and lysine residues of angiogenin are required for both angiogenic and ribonucleolytic activities (Shapiro et al., 1986, Biochemistry 25: 3527-3532; Shapiro et al., 1987b, Proc. Natl. Acad. Sci. U.S.A. 84: 8783-8787; Shapiro et al., 1988b, Biochem. Biophys. Res. Commun. 156: 530-536; Shapiro et al., 1989, Biochemistry 28: 1726-32; and Shapiro and Vallee, 1989, Biochemistry 28: 7401-8). However, additional molecular features must be critical to angiogenesis, since bovine pancreatic RNase A contains the corresponding histidine and lysine residues yet it is not angiogenic. Such additional molecular features, if they could be identified, should include individual residues and/or regions of sequence which are unique to angiogenin. Harper and Vallee, 1989, Biochem. 28: 1875-84 have recognized that one striking structural difference between angiogenin and RNase is the virtual absence of sequence similarity within the region of RNase that contains the Cys-65-Cys-72 disulfide bond. Angiogenin lacks this disulfide linkage. Having identified this region of angiogenin, Harper and Vallee, 1989, supra, have described a novel genetically-engineered covalent angiogenin/RNase hybrid protein, ARH-I, wherein the segment of angiogenin comprising amino acid residues 58-70 was replaced by the corresponding segment (residues 59-73) of RNase A. The genetically-engineered replacement of this segment of angiogenin by the corresponding segment from RNase A resulted in a covalent hybrid protein with characteristics more like RNase A. ARH-I exhibited dramatically increased RNase-like enzymatic activity but a markedly decreased angiogenic biological activity. Harper and Vallee, 1989, supra, were unable to prepare or identify a hybrid protein with increased angiogenic biological activity. Such a hybrid would be unexpected in view of their experimental design to insert an RNase-unique region into angiogenin.

SUMMARY OF THE INVENTION

It has now been unexpectedly found that replacement of an angiogenin-unique segment of angiogenin comprising N-terminal amino acids at or corresponding to residues 8-22 of angiogenin with the corresponding segment (residues 7-21) of RNase A has resulted in a novel recombinant hybrid protein with increased angiogenic potency.

According to the present invention, an N-terminal region of angiogenin was identified as a possible candidate region unique to angiogenin and thus implicated as critical for angiogenin-specific activities. This region was (1) very highly conserved in the amino acid sequence of angiogenin across four species (human, bovine, porcine and lapine), and (2) different from the corresponding region of RNases. The novel recombinant covalent angiogenin/RNase hybrid of the present invention, ARH-III, thus comprises a modified angiogenin in which a segment near the N-terminus (residues 8-22) of angiogenin was replaced by regional mutagenesis with the corresponding segment of RNase A (residues 7-21). This novel recombinant hybrid exhibited a 10-fold more potent angiogenic activity and, increased binding (by at least one order of magnitude) to the placental ribonuclease inhibitor (PRI) as compared with angiogenin. The ribonucleolytic activity of ARH-III was unchanged toward most substrates. However, the capacity of ARH-III to inhibit cell-free protein synthesis was decreased 20-30 fold as compared with that of angiogenin. Thus, this novel hybrid protein containing a pentadecapeptide segment of RNase A is biologically more active than angiogenin itself, in fact, is an enhanced angiogenin.

BRIEF DESCRIPTION OF THE DRAWINGS

FIG. 2a shows the N-terminal amino acid sequences of RNase A, human angiogenin, and ARH-III. Residues in RNase A conserved in pancreatic RNase from 39 mammalian species are indicated by an asterisk. Boxed residues in angiogenin are conserved in the human, bovine, porcine, and lapine proteins. FIG. 2b shows the DNA sequence of the synthetic double-stranded oligonucleotide encoding residues 4-23 of ARH-III used as Fragment B in the construction of the ARH-III coding sequence as described in Example 2.

FIG. 9 is a ribbon diagram of RNase A.

DETAILED DESCRIPTION

Figure 1:
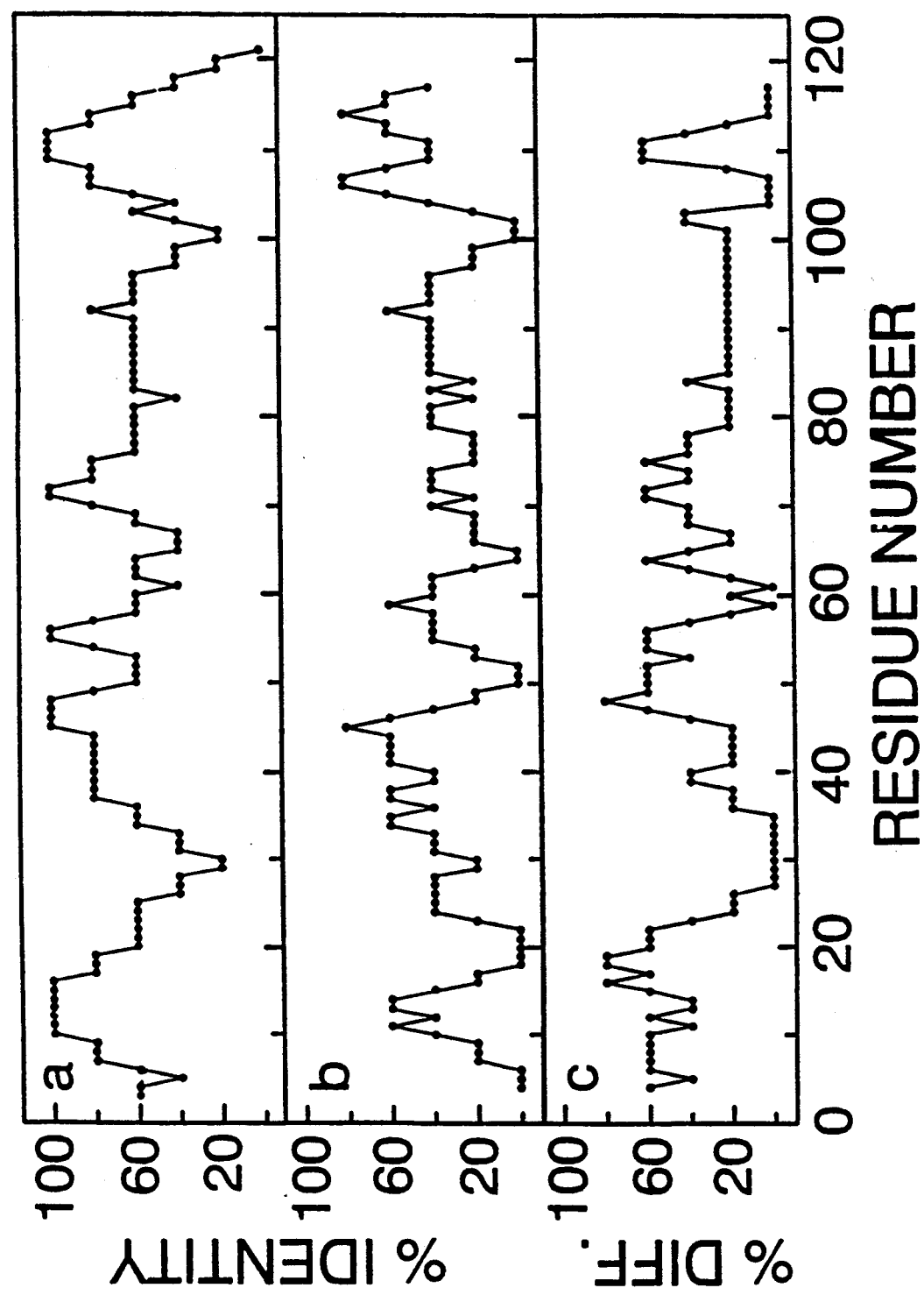
FIGS. 1a and 1b are graphs showing the percent identity of amino acid sequence by residue number of human angiogenin as compared to that of bovine angiogenin (FIG. 1a) and RNase A (FIG. 1b) in order to determine an angiogenin-unique segment as described in Example 1.
FIG. 1c is a graph showing the difference in percent identity between FIGS. 1a and 1b.

Prior to setting forth the invention, it may be helpful to define certain terms used herein.

Biological activity, is a function or set of functions performed by a molecule in a biological context (i.e., in an organism or an in vitro facsimile). For angiogenin, biological activity is characterized by its angiogenic activity (angiogenesis). It may also include second messenger and/or ribonucleolytic activity.

Angiogenic activity, is the chemical stimulation of hemovascular development in tissue. It is generally associated with diffusible substances produced by a variety of cell types. Angiogenic activity may be characterized by a positive response in the chick embryo chorioallantoic membrane assay (Knighton et al., 1977, Br. J. Cancer 35:347-356) and/or the rabbit cornea implant assay (Langer and Folkman, 1976, Nature 263:797-800).

Ribonucleolytic activity is the enzymatic cleavage of RNA, including the limited catalytic cleavage of rRNA and tRNA.

A mutant gene or a DNA construct is a DNA molecule, or a clone of such a molecule, which has been modified by human intervention to contain segments of DNA which are changed, combined or juxtaposed in a manner which would not otherwise exist in nature.

A mutant (mutated) angiogenin protein is an angiogenin protein or any peptide fragment of that protein in which one or more amino acids have been replaced with other amino acids, and which has altered biological activity when compared with non-mutated or wild-type angiogenin.

Preferred prokaryotic host cells for use in carrying out the present invention are strains of the bacteria *Escherichia coli*, although Bacillus and other genera are also useful. Techniques for transforming these host cells and expressing foreign genes cloned in them are well known in the art (see, for example, Maniatis et al., 1982, *Molecular Cloning: A Laboratory Manual*, Cold Spring Harbor Laboratory, Cold Spring Harbor, New York; *Current Protocols in Molecular Biology*, 1987 (updated through 1989), Ausubel et al., (eds.), Greene Publishing Associates and Wiley-Interscience, New York; Perbal, 1988, *A Practical Guide to Molecular Cloning*, John Wiley & Sons, New York; Davis et al., 1986, *Basic Methods in Molecular Biology*, Elsevier Science Publishing Co., New York). Vectors used for expressing foreign genes in bacterial host cells will generally contain a selectable marker, such as a gene for antibiotic resistance, and a promoter which functions in the host cell. Appropriate promoters include the trp (Nichols and Yanofsky, 1983, Meth. in Enzymology 101:155) lac (Casadaban et al., 1980, J. Bact. 143: 971-980) and phage λ promoter systems. Plasmids useful for transforming bacteria include pBR322 (Bolivar, et al., 1977, Gene 2:95-113), the pUC plasmids (Messing, 1983, Meth. in Enzymology 101:20-77; and Vieira and Messing, 1982, Gene 19:259-268), pCQV2 (Queen, 1983, J. Mol. Appl. Genet. 2: 1-10), and derivatives thereof.

Eukaryotic microorganisms, such as the yeast *Saccharomyces cerevisiae*, may also be used as host cells. Techniques for transforming yeast are also known in the art (see, for example, Strathern et al., 1982, *The Molecular Biology of the Yeast Saccharomyces*, 2 vols. Cold Spring Harbor Laboratory, New York; Perbal, 1988, supra; Davis et al., 1986, supra; Beggs, 1978, Nature 275: 104-108). Expression vectors for use in yeast include YEp13 (Broach et al., 1979 Gene 8:121-133), YRp7 (Struhl et al., 1979, Proc. Natl. Acad. Sci. USA 76:1035-1039), pJDB248 and pJDB219 (Beggs, ibid), and derivatives thereof. Such vectors will generally comprise a selectable marker, such as the nutritional marker TRP, which allows selection in a host strain carrying a trp1 mutation. Preferred promoters for use in yeast expression vectors include promoters from yeast glycolytic genes (Hitzeman et al., 1980, J. Biol. Chem. 255: 12073–12080; Alber and Kawasaki, 1982, J. Mol. Appl. Genet. 1:419–434) or alcohol dehydrogenase genes (Young et al., in *Genetic Engineering of Microorganisms for Chemicals*, Hollaender et al., eds., p. 335, Plenum, New York, 1982; and Ammerer, Meth. in Enzymology 101:192–201, 1983). To facilitate purification of an angiogenic protein produced in a yeast transformant and obtain proper disulfide bond formation, a signal sequence, preferably from a yeast gene encoding a secreted protein, may be joined to the coding sequence for the angiogenic protein. A particularly preferred signal sequence is the pre-pro region of the MFα1 gene (Kurjan and Hershowitz, 1982, Cell 30:933–943).

Higher eukaryotic cells may also serve as host cells in carrying out the present invention. Cultured mammalian cells are preferred. Expression vectors for use in mammalian cells will comprise a promoter capable of directing the transcription of a foreign gene introduced into a mammalian cell. A particularly preferred promoter is the mouse metallothionein-1 (MT-1) promoter (Palmiter et al., 1983, Science 222:809–814). Also contained in the expression vectors is a polyadenylation signal, located downstream of the insertion site. The polyadenylation signal may be that of the cloned angiogenic protein gene, or may be derived from a heterologous gene. Other genomic sequences (for example, intron sequences) may be inserted which enhance expression.

Cloned gene sequences may then be introduced into cultured mammalian cells by methods known in the art, for example, calcium phosphate-mediated transfection (Wigler et al., 1978, Cell 14:725; Coraro and Pearson, 1981, Somatic Cell Genetics 7:603; Graham and Van der Eb, 1973, Virology 52:456). A precipitate is formed of the DNA and calcium phosphate, and this precipitate is applied to the cells. Some of the cells take up the DNA and maintain it inside the cell for several days. A small fraction of these cells (typically $10^{-4}$) integrate the DNA into the genome. In order to identify these integrants, a gene that confers a selectable phenotype (a selectable marker) is generally introduced into the cells along with the gene of interest. Preferred selectable markers include genes that confer resistance to drugs, such an neomycin, hygromycin, and methotrexate. Selectable markers may be introduced into the cell on a separate plasmid at the same time as the gene of interest, or they may be introduced on the same plasmid.

The copy number of the integrated gene sequence may be increased through amplification by methods known in the art using certain selectable markers (e.g., dihydrofolate reductase, which confers resistance to methotrexate). The selectable marker is introduced into the cells along with the gene of interest, and drug selection is applied. The drug concentration is then increased in a step-wise manner, with selection of resistant cells at each step. By selecting for increased copy number of cloned sequences, expression levels may be substantially increased.

Mutant angiogenin proteins produced according to the present invention may be used to produce pharmaceutical compositions for therapeutic or diagnostic use by combining them with suitable carriers. These pharmaceutical compositions containing an effective angiogenic amount of the protein are within the scope of this invention. Such pharmaceutical compositions may be used to promote or influence the development of a hemovascular network in mammals, such as cats, dogs, and humans, for example, to induce collateral circulation following a heart attack or other ischemic heart diseases. For this purpose, the angiogenin protein of this invention is administered parenterally. The term "parenterally" as used herein includes subcutaneous, intravenous, intramuscular, or intrasternal injection or infusion techniques. Among the acceptable vehicles and solvents that may be employed are, for example, "Water for Injection," Ringer's solution and isotonic sodium chloride solution. In a typical practice, the selected protein is dissolved in a vehicle, typically Water for Injection, and compounded into parenteral preparations employing known pharmaceutical art with each dosage unit containing an effective angiogenic amount of the protein. The effective dose needs to be individualized by the clinician until the desired clinical effect has been reached.

To broaden their therapeutic spectrum, these pharmaceutical compositions may be administered concomitantly with other drugs such as beta-adrenoceptor antagonists, for example, propranolol, calcium channel blockers, for example, nifedipine or other coronary vasodilators.

The proteins of this invention may also be used to promote wound healing, for example in joints or other locations containing soft tissues. For example, if injury occurs to the meniscus of the knee or shoulder as frequently occurs in sports-related injuries or osteoarthritis, time release implants of therapeutically effective amounts of the angiogenin protein at the site of injury is a preferred treatment for healing of torn or traumatized fibrocartilage material. The proteins of this invention may also be administered topically to the wound site. For topical application, the selected angiogenic protein of this invention is mixed with a dermatologically acceptable carrier such as petroleum jelly, talc, and the like and applied liberally to the affected site. Regional mutagenesis with recombinant DNA technology provides a superior method for the production of mutant proteins according to the present invention in the quantities needed for these therapeutic applications.

It is well known that angiogenin and RNase A display similarities in amino acid sequence, three-dimensional structure, and capacity to cleave RNA. Despite this, RNase A is not angiogenic, does not induce a second messenger response with endothelial cells (Bicknell & Vallee, 1988, Proc. Natl. Acad. Sci. USA 85: 5961–5965), and does not display selective cleavage of rRNA in intact ribosomes (St. Clair et al., 1987, Proc. Natl. Acad. Sci. USA 84: 8330–8334; St. Clair et al., 1988, Biochemistry 27: 7263–7268). Since the in vivo and in vitro activities of angiogenin clearly differ from those of RNase A, the molecular features which form the bases of these activities should also differ. To identify such features, the naturally occurring sequence variation in angiogenins from different species were analyzed as described in Example 1. Regions of angiogenin which are critical to its unique activities (i) should be conserved across species, and (ii) should be different from the corresponding regions of the RNases. If such regions can be identified, as according to Example 1, the actual role of these regions can be examined by means of regional mutagenesis as described in Example 2.

Similarity plots were constructed comparing the sequence of human angiogenin with that of bovine angiogenin (FIG. 1a) and that of bovine pancreatic RNase A (FIG. 1b). The difference between the two plots, 1a minus 1b, was then calculated in order to elucidate those regions of human angiogenin with both high identity to bovine angiogenin and low identity to RNase A (FIG. 1c). From this analysis, one segment stood out; this was a segment centered at residues 16-19. Since the analysis employed a five residue "window," the actual amino acids involved are Tyr-14 through Arg-21. In the three-dimensional structure these residues (except for Tyr-14) would be in an extended conformation stretching away from the active site, based on comparison to RNase A (FIG. 9). Further inspection of this amino acid sequence (FIG. 2a) revealed that six of the eight residues in this segment are conserved in the mammalian angiogenins sequenced thus far. Only one of these 8 residues, Asp-15, is also present in RNase A. Thus, while this sequence is highly conserved in the angiogenins, the corresponding sequence in the pancreatic RNases is very poorly conserved across species (FIG. 2a). In fact, Hofmann et al., 1966, J. Amer. Chem. Soc. 88: 3633-3639, have shown that residues 15-20 are completely nonessential to RNase A activity.

Immediately preceding residues 14-21 of angiogenin is a block of amino acids from His-8 to His-13 which is conserved in four mammalian angiogenins (FIG. 2a). Residues 8-13 form part of an α-helix which begins at Ser-4, assuming a similar structure to RNase A (FIG. 9). Two residues, His-8 and Thr-11, replace amino acids conserved in 39 mammalian pancreatic RNases, and the acidic Glu-9 of RNase A is replaced by a hydrophobic leucine. Therefore, these residues from His-8 to His-13 also showed potentially significant differences from RNase A. According, in order to elucidate the functional role of this entire section of angiogenin, residues 8 to 21 were investigated along with residue 22 (in order to maintain the original net charge of the protein) by means of regional mutagenesis.

Regional mutagenesis differs from site-directed mutagenesis in that a segment or region of amino acids is replaced, rather than a single residue. This enables testing of multiple residues simultaneously, and also allows for examination of secondary structure contributions. Because of the three-dimensional similarities between angiogenin and RNase A, when select regions are interchanged from one protein to the other, the overall conformation may be maintained. The efficacy of this approach was demonstrated previously when residues 58-70 of angiogenin were replaced by RNase A residues 59-73 (Harper and Vallee, 1989, Biochemistry 28: 1875-1884). The resulting mutant hybrid protein, designated ARH-I, folded into the correct conformation, forming not only the 3 disulfide bonds found in angiogenin, but the fourth disulfide bond from RNase A as well. Thus, the N-terminal region of angiogenin might also be amenable to replacement while maintaining overall conformation, particularly in light of the fact that the peptide Ang(1-21) comprising amino acid residues 1-21 of angiogenin has been shown to bind non-covalently to the peptide RNase(21-124) comprising amino acid residues 21-124 of RNase with a micromolar dissociation constant, reconstituting 50% of the enzymatic activity of RNase A (Harper et al., 1988, Biochemistry 27: 219-226). This demonstrated that there was a structural resemblance between the two proteins in this region. The amino-terminal region of RNase A has been the subject of extensive crystallographic and chemical studies, due largely to the elaboration of S-peptide/S-protein system. The term S-peptide refers to the peptide of RNase comprising residues 1-20, generated by limited subtilisin proteolysis of RNase A. The remainder of the molecule comprising residues 21-124, is referred to as S-protein (Richards and Vithayathil, 1959, J. Bio. Chem. 234: 162-166). FIG. 9 shows a ribbon diagram of RNase A, highlighting positions of essential active site residues His-12, Lys-41 and His-119. Also highlighted are Lys-7 and Ser-21. As shown in FIG. 9, residues 3-13 of RNase A form an α-helix that borders the active site cleft and contains the catalytic His-12 and substrate-binding Gln-11 residues; the helix binds non-covalently to the S-protein part of the molecule with a submicromolar dissociation constant (Richards & Wyckoff, 1971, Enzymes (3rd Ed.) 4: 647-806 and references therein). Residues 15-23 then extend around the outside of the molecule away from the active site, and form a juncture with a second α-helix. Many of the residues have been assigned specific functions (summarized in Richards and Wyckoff, 1971, supra; Richards and Wyckoff, 1973, Atlas of Molecular Structures in Biology (Phillips, D. C. & Richards, F. M., Eds.) vol. 1, Oxford University Press, London; Blackburn & Moore, 1982, Enzymes (3rd Ed.) 15: 317-433; Wlodawer et al, 1982, J. Biol. Chem. 257: 1325-1335), including Glu-2 (side-chain hydrogen bonds (H-bonds) to Arg-10), Phe-8 (hydrophobic interaction with protein core), Arg-10 (side-chain H-bonds to Glu-2), Gln-11 (side-chain H-bonds to substrate phosphate; backbone carbonyl H-bonds to Asn-44), His-12 (side-chain involved in catalysis; H-bonds to carbonyl of Thr-45), Met-13 (hydrophobic interaction with protein core) and Asp-14 (side-chain H-bonds to Tyr-25 and/or Arg-33). The importance of these residues is reflected in the fact that, with the exception of Met-13, all are conserved in the pancreatic RNases of 39 different mammalian species (Beintema et al., 1986, Mol. Biol. Evol. 3: 262-275). In contrast, none of the residues from 15-23 are conserved among these different RNases, and as discussed above, residues 15-20 are completely nonessential.

The amino-terminal region of angiogenin, by comparison, has not been extensively studied. However, recently, amino acid sequence analysis of the angiogenin of several species has been completed. The sequence of the N-terminal region of angiogenin is shown in FIG. 2a; residues conserved in 4 different species are boxed. Sequence analysis of the angiogenin from these various species revealed that sixteen of the first twenty-one residues of angiogenin are invariant, and 12 of the 16 are different from their counterpart residues in RNase A. Several amino acids that are conserved in all the pancreatic RNases are replaced in angiogenin; these are Glu-2, Ala-5, Lys-7, and Arg-10. Based on comparison with the structure of RNase A, residues 4-14 of angiogenin would form an α-helix with the side chains of Gln-12 and His-13 directed into the active site cleft. Residues 15-24 would then stretch in a relatively unordered configuration toward the "back" of the molecule, behind several strands of β-sheet, to a juncture with a second α-helix. The region selected for mutation according to the present invention, covered residues 8-22 of angiogenin and corresponded to the sequence of RNase A spanning residues Lys-7 to Ser-21, as highlighted in FIG. 9. The construction of the DNA coding sequence for this genetically-engineered hybrid protein, designated ARH-III, is described in Example 2. The coding sequence for ARH-III was expressed in E. coli host cells and the ARH-III protein was purified as described in Example 3. The coding sequence for ARH- III may also be expressed in host cells other than bacteria, such as yeast or mammalian cells, as described above. The amino acid analysis and tryptic peptide analysis (Example 4) of the ARH-III protein purified from the *E. coli* expression system were consistent with the successful replacement of residues 8-22 of angiogenin with residues 7-21 of RNase A, as well as the removal of Met-(−1)from the *E. coli* expressed protein.

Figure 5:
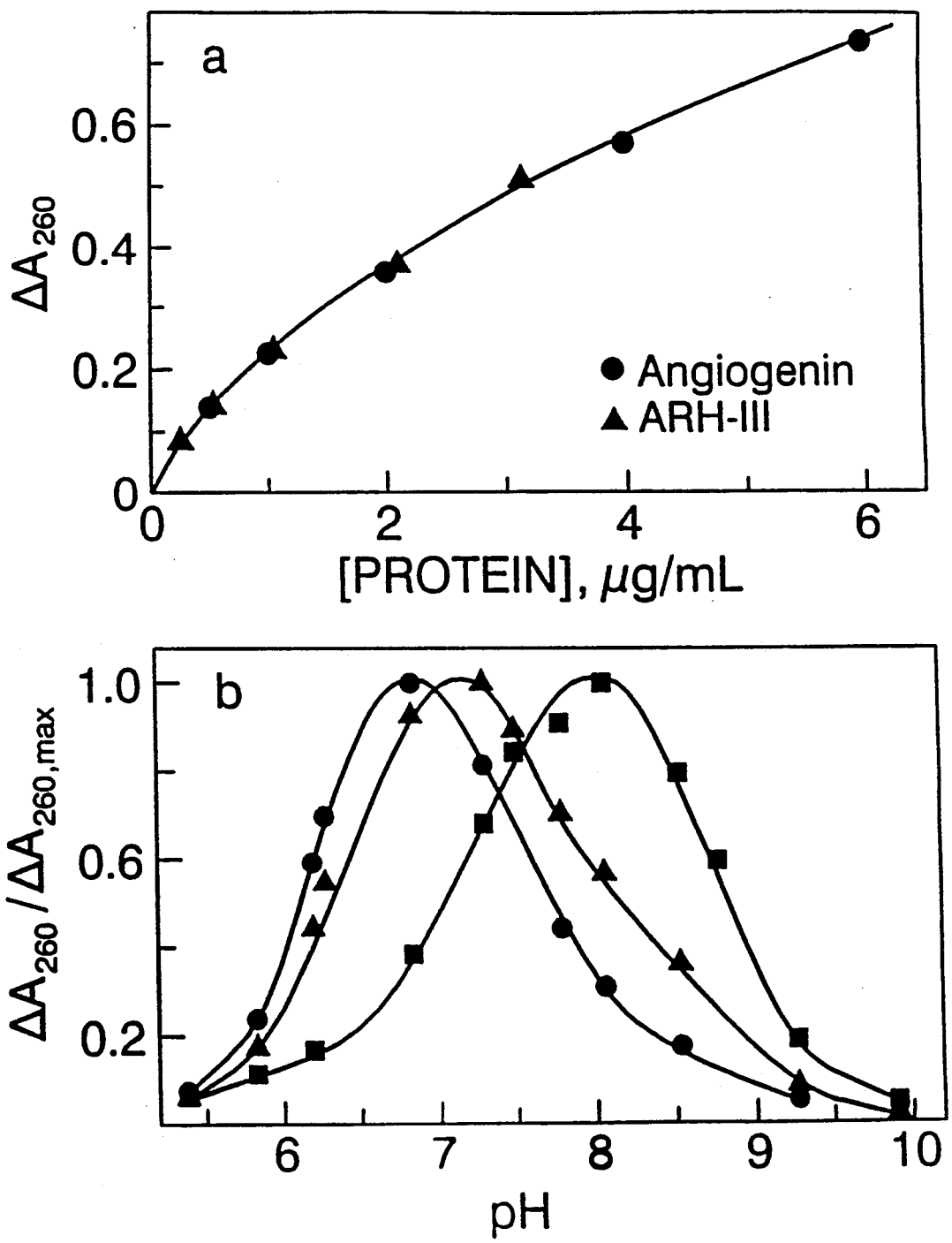
FIG. 5a is a graph showing the activity of angiogenin and ARH-III toward yeast tRNA.
FIG. 5b is a graph showing the effects of pH on activities of ARH-III as compared with angiogenin and RNase as described in Example 5.

The regional mutation had little effect on the activities of the hybrid protein, ARH-III, toward most RNA substrates as described in Example 5. At pH 6.8, ARH-III cleaved tRNA at a rate identical to that of angiogenin (FIG. 5a), although there was a slight shift in the pH optimum (FIG. 5b). Rates of cleavage of isolated 18S and 28S rRNA as well as the dinucleotide RNA substrates (obtained from Sigma Chemical Co. or Calbiochem-Behring) cytidylyl-(3'-5') adenosine (CpA), cytidylyl-(3'-5') guanosine (CpG), uridylyl-(3'-5') adenosine (UpA), and uridylyl-(3'-5') guanosine (UpG) (Table II) were also essentially the same as those for angiogenin. Accordingly, the replaced region did not appear to play a significant role in these activities in angiogenin. Moreover, these results suggest that the relative differences in dinucleotide preference which exist between angiogenin and RNase A (Shapiro et al., 1988, Anal. Biochem. 175: 450-461; Harper & Vallee, 1989, Biochemistry 28: 1875-1884) probably do not stem from substrate-enzyme interactions with any of these residues. The lack of an effect on the general RNase activities does not preclude a role for ribonucleolytic cleavage in angiogenin's mechanism of action, but rather suggests that such cleavage would involve a specific substrate.

Figure 6:
FIG. 6 is an autoradiograph of a urea-polyacrylamide gel showing the effects of angiogenin and ARH-III on intact ribosomes as described in Example 6.
Figure 6:
Figure 6:
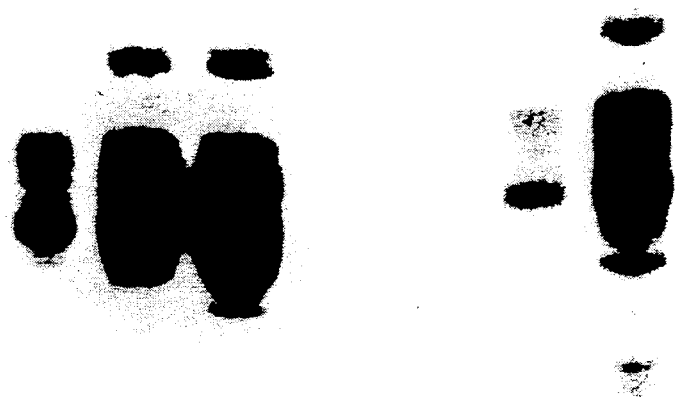
Figure 7:
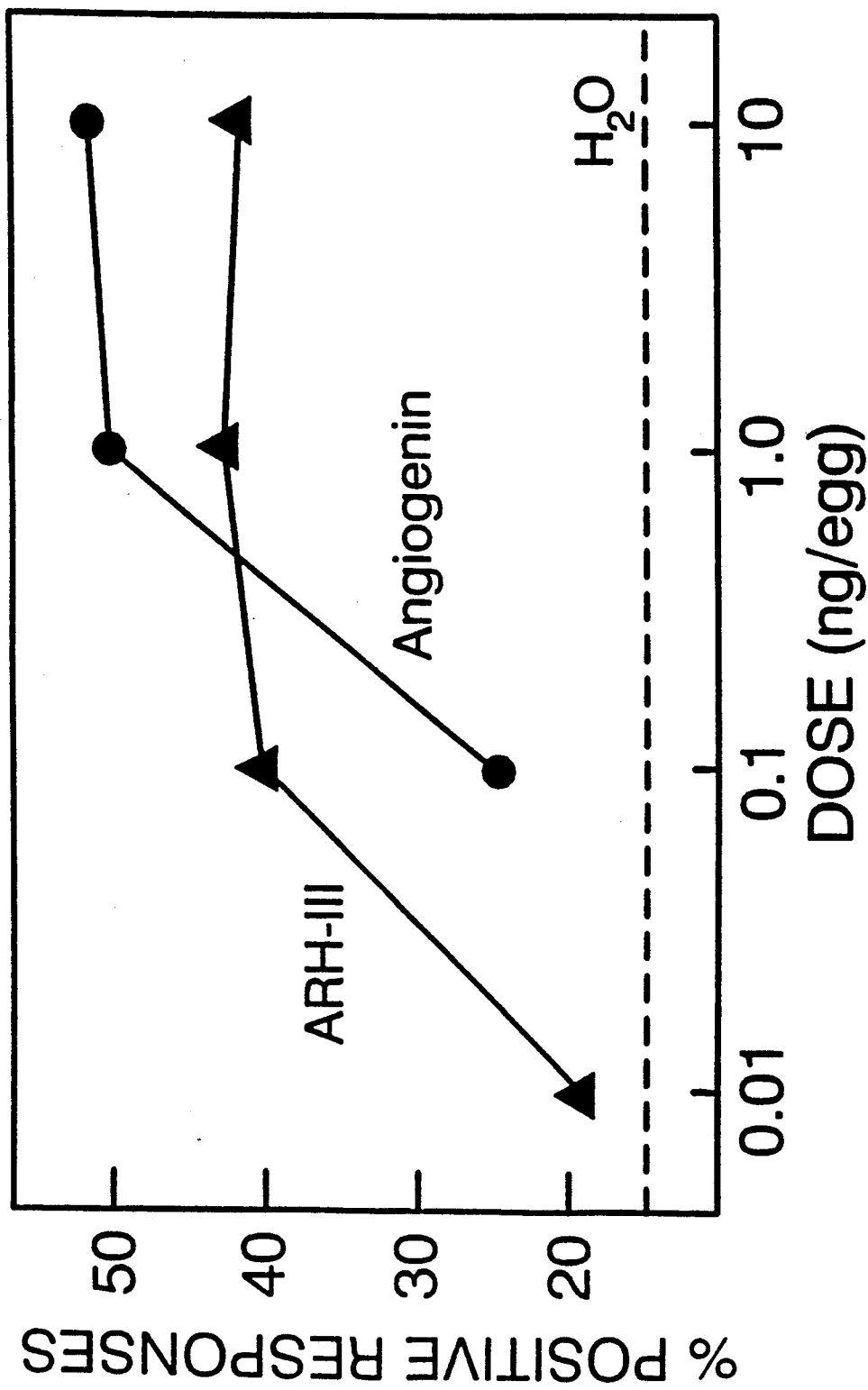
FIG. 7 is a graph showing the activities of ARH-III and angiogenin in the CAM assay as described in Example 7.

In contrast, as described in Example 6, the regional mutation had significant effects on the activities of ARH-III in protein synthesis inhibition and angiogenesis, and also in second messenger assays. ARH-III was approximately 30-fold less active than angiogenin in inhibiting cell-free protein synthesis; the effects were observed both on the incorporation of $^{35}$S-methionine into whole protein (Table III), and on the generation of specific rRNA cleavage productions from intact ribosomes (FIG. 6). In the CAM angiogenesis assay, as described in Example 8, ARH-III was unexpectedly more potent than angiogenin by a factor of ten (FIG. 7). ARH-III reached full activity at 0.1 ng per egg whereas angiogenin typically required 1 ng (FIG. 7). Similar results were observed in second-messenger assays with endothelial cells. Dose response curves for the ARH-III induced release of diacylglycerol or secretion of prostacyclins were shifted to lower concentrations by 10- to 100-fold compared to those for angiogenin.

The lack of correlation between the effects of the regional mutation on angiogenesis (10-fold increase in potency) and those on protein synthesis inhibition (30-fold decrease in potency) suggests that these two activities are not linked. These two activities may represent separate, unrelated functions of the angiogenin molecule. Conversely, the correlation between the effects of the regional mutation on angiogenesis and second-messenger activity indicates that these two activities of angiogenin may be linked. For these two activities (angiogenesis and second-messenger), the dose response curve for ARH-III shifts to lower concentrations by 10- to 100-fold, compared to angiogenin. These data support the hypothesis that the linkage between these two activities may involve activation of a putative angiogenin receptor.

As described in Example 8, ARH-III exhibited one order of magnitude increased binding to PRI as compared with angiogenin. PRI is a tight-binding inhibitor of angiogenin and RNases. This 50 kDa protein binds to angiogenin with a $K_i$ of 0.7 fM (Lee et al., 1989b, Biochemistry 28: 225-230). Interaction minimally encompasses the active site and perturbs the region around Trp-89 (Lee et al., 1989a, Biochemistry 28: 219-224; Lee & Vallee, 1989a, Biochemistry 28: 3556-3561). The interaction of PRI with RNase A, which is 60-fold weaker than that with angiogenin (Lee et al., 1989b. Biochem. Biophys. Res. Commun. 161: 121-126,) is reported to take place only within the S-protein part of the molecule, with no significant contribution from residues 1-20 (Blackburn & Jailkhani, 1979, J. Biol. Chem. 254: 12488-12493). It is therefore surprising that regional mutation of angiogenin residues 8-22 according to the present invention actually increased the affinity of ARH-III for PRI as shown in Table V. The association rate more than doubled, and the dissociation rate was decreased to the limit of detection, i.e., at least four-fold. Consequently, the $K_i$ is at least an order of magnitude lower than that for angiogenin. This change is unexpected in view of the enhanced angiogenic and cellular response activity of ARH-III at low concentrations.

In the present invention, as with any investigation involving mutagenesis, the question arises as to the proper refolding of the mutant protein. The evidence for an undistorted conformation for the ARH-III regional mutant is three-fold: (1) all three of the disulfide bonds formed correctly, which requires precise alignment of six cysteine residues from widely separate locations in the sequence; (2) the rates of hydrolysis of four dinucleotides and other RNA substrates are unaffected by the regional mutation, meaning that positions of the different residues directly involved in phosphodiester bond cleavage were not distorted; and (3) ARH-III binds extremely tightly to PRI; this interaction again requires the exact three-dimensional placement of multiple residues which are involved in binding, and the low $K_i$ value ($\leq 7 \times 10^{-17}$M) is inconsistent with any large alterations in conformation.

The results described in the examples that follow demonstrate that the characteristic angiogenin activities of the novel angiogenin/RNase hybrid protein ARH-III of the present invention were affected dramatically by the regional mutagenesis described herein. The invention is thus further illustrated by the following examples, which are not to be construed as limiting the invention in scope or spirit to the specific procedures described in them.

EXAMPLE 1

Selection of a Region for Mutagenesis

Similarity plots were computed to provide a quantitative means of comparing the sequence of human angiogenin with that of bovine angiogenin (FIG. 1a) and RNase A (FIG. 1b). The plots show the percent identity between two proteins within a moving five residue window centered at the human angiogenin residue indicated. This was accomplished using a computer program courtesy of Dr. D. J. Strydom, Harvard Medical School. In order to facilitate alignment of the sequences, the N-terminal alanine of bovine angiogenin was deleted, as were RNase A residues Asn-24, Arg-39, Gln-69, Thr-70, Pro-114 and Tyr-115 (RNase A numbering). Because values were averaged over five residues, the plots emphasize regional trends rather than similarities/differences at individual sites.

The first plot compares the sequence of human angiogenin with that of bovine angiogenin (FIG. 1a). In most instances, the identity was 60% or greater, consistent with an overall identity of 64% (Maes et al., 1988, FEBS Lett. 241: 41–45; Bond and Strydom, 1989, Biochemistry 28: 6110–6113). Not surprisingly, the regions around the three essential catalytic residues of angiogenin, His-13, Lys-40, and His-114, were highly similar between the proteins; in fact, the three longest segments of 80% identity or higher occur at positions 7–19, 37–48, and 106–114. Five different regions showed 100% identity, and the longest was that segment from positions 10–16.

FIG. 1b compares human angiogenin with RNase A. The degree of similarity was much lower in general than that observed above, consistent with the overall sequence identity of 33%. In this case, it is actually the differences between these two sequences that hold the most interest, since they may underlie the different biological roles of the proteins. Short regions of least similarity (0% identity) occurred at positions 4–6, 50–52, 64–65, and 100–102; the longest region was from 18–22.

FIG. 1c shows the difference of the two above figures, calculated by subtracting values from FIG. 1b from the corresponding values in FIG. 1a. High values in FIG. 1c indicate areas of human angiogenin with *both* high identity to bovine angiogenin and low identity to RNase A. These are regions most likely to be involved in a unique role for angiogenin. Only four individual windows reach a difference in identity of 80%, and three of them occur in close proximity at positions 16, 18 and 19. Thus, this one small segment stands out as the most conserved in the angiogenins and the most different from RNase A. The residues encompassed in this segment, including all those within the two end windows, are Tyr-14 through Arg-21.

FIG. 2a shows the N-terminal sequences of RNase A and human angiogenin. Residues in RNase A conserved in pancreatic RNase from 39 mammalian species (Beintema et al., 1986, Mol. Biol. Evo. 3: 262–275) are indicated by an asterisk. Boxed residues in angiogenin are conserved in the human, bovine (Bond and Strydom, 1989, Biochemistry 28: 6110–6113; Maes et al., 1988, FEBS Lett. 241: 41–45), porcine, and lapine proteins. <Q is pyroglutamic acid. In particular, FIG. 2a shows that immediately preceding residues 14–21 of angiogenin is a block of amino acids from His-8 to His-13 which is conserved in four mammalian angiogenins; the residues form part of an α-helix which begins at Ser-4, assuming a similar structure to RNase A as shown in FIG. 9. Two residues, His-8 and Thr-11, replace amino acids conserved in 39 mammalian pancreatic RNases, and the acidic Glu-9 of RNase A is replaced by hydrophobic leucine. Therefore, these residues also showed potentially significant differences from RNase A. Accordingly, in order to elucidate the functional role of this entire section of angiogenin, residues 8 to 21 were investigated along with residue 22 (in order to maintain the original net charge of the protein) by means of regional mutagenesis.

EXAMPLE 2

Construction of the ARH-III Coding Sequence

Figure 3:
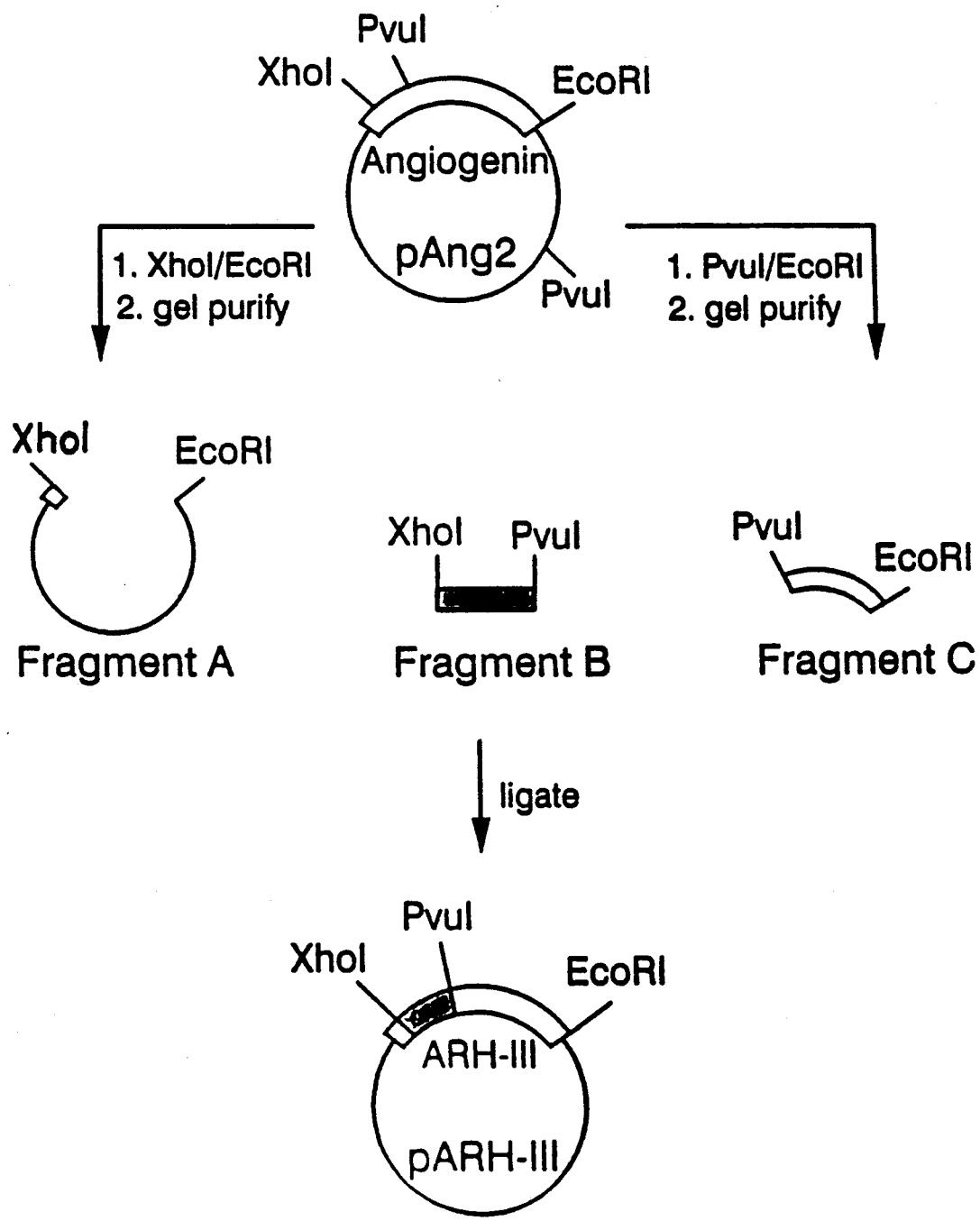
FIG. 3 is a diagram of the construction of the coding sequence for ARH-III as described in Example 2.

The entire section of angiogenin selected for mutagenesis according to Example 1 extends from His-8 to Asp-22. These residues were replaced by residues 7–21 of RNase A (FIG. 2a). The DNA coding sequence for the hybrid protein, designated ARH-III (FIG. 2a,b), was constructed as shown in FIG. 3 as follows. Fragments A and C were generated by cleavage of pAng2 DNA (13 μg) with either XhoI and EcoRI, or PvuI and EcoRI, followed by purification by electrophoresis in 3% gels using NuSieve GTG low melting point agarose (obtained from FMC BioProducts). DNA from the expression plasmid pAng2 was obtained as described by Shapiro et al., 1988, Anal. Biochem. 175: 450–461 and U.S. patent application Ser. No. 305,968 which is hereby incorporated by reference. Plasmid pAng2 contains a modified Trp promoter and ampicillinase marker for selection. Fragment A (2928 bp) contained the entire noncoding region of the plasmid and the coding region for Met-(−1) through Asn-3; fragment C consisted of the coding region from Arg-24 through Pro-123 and the two stop codons. Fragments A and C were then ligated with fragment B, a synthetic double-stranded oligonucleotide coding for residues 4–7 of angiogenin, 7–21 of RNase A, and 23 of angiogenin as shown in FIG. 2b. The termini of this synthetic oligonucleotide are compatible for ligation of XhoI and PvuI restriction enzyme cleavage sites. This synthetic double-stranded oligonucleotide was obtained from the Biopolymer Laboratory, Dept. of Biological Chemistry and Molecular Pharmacology, Harvard Medical School. Each strand was synthesized according to conventional methods using β-cyanoethyl phosphoramidite automated synthesis, by a Milligen Synthesizer (Matteucci and Caruthers, 1981, J. Amer. Chem. Soc. 103: 3185–3191; Beaucage and Caruthers, 1981, Tet. Letters 22: 1859–1862). The duplex was obtained by annealing the 5′ phosphorylated complementary oligomers as described by Harper & Vallee, 1989, Biochemistry 28: 1875–1884. The most successful ligation reaction employed 24, 150 and 100 pmol of fragments A, B and C, respectively, and 6 units T4 DNA ligase in a 60 μL volume; the final agarose concentration was 1.4%. *E. coli* strain W3110 cells were then transformed using the $CaCl_2$ procedure (Maniatis et al., 1982, *Molecular Cloning: A Laboratory Manual*, Cold Spring Harbor Laboratory, Cold Spring Harbor, N. Y.) and plasmid uptake detected by ampicillin resistance.

Both restriction enzyme mapping (with HaeIII or with EcoRI and KpnI) and nucleotide sequencing analysis were employed to ensure that the new genetically-engineered plasmid, designated pARH-III, contained the correct coding sequence. DNA sequencing was performed with a Sequenase ™ kit (U.S. Biochemical Corp.) with [$^{35}$S]-deoxyadenosine-5′-(α-thio)triphosphate. For sequencing, the KpnI-EcoRI fragment containing the coding region was isolated and cloned into M13mp18 using conventional methods. The nucleotide sequence corresponding to the first 60 amino acids of the protein was as expected for the hybrid protein. Plasmid pARH-III has been deposited with the American Type Culture Collection (A.T.C.C.) under accession no. 68188.

EXAMPLE 3

Expression and Purification of Angiogenin and ARH-III

A. Angiogenin

Large-scale expression in bacterial host cells and purification of angiogenin were performed as described in detail by Shapiro et al., 1988, Anal. Biochem., 175: 450–461. Briefly, *E. coli* strain W3110 cells containing pAng2 were grown in supplemental M9 medium and then induced by addition of indole-3-acrylic acid. Cells were then collected by centrifugation, suspended in a lysozyme, NaCl, EDTA solution for 45 minutes and then sonicated. Insoluble angiogenin was recovered by centrifugation, solubilized in guanidine.HCl and 2-mercaptoethanol, and then refolded by dilution into Tris-NaCl buffer. After concentrating in an Amicon (Danvers, Mass. 01923) pressure filtration unit, the angiogenin was purified by sequential application to Mono S and C18 reversed phase HPLC columns. In addition, angiogenin was obtained from genetically-engineered baby hamster kidney (BHK) cells as described in detail by Kurachi et al., 1988, Biochemistry 27: 6557–62. Briefly, the transfected cells were cultured at 37° C. in DME medium containing 80 μM $ZnSO_4$, and 2 μM $CdSO_4$, which was exchanged at 2–3 day intervals. Angiogenin was then purified from the media by sequential chromatographies on CM-cellulose ion exchange and Mono S columns. Unless otherwise noted, the angiogenin used in the examples which follow was obtained from the BHK cells as summarized.

B. ARH-III

The levels of expression of 9 individual colonies of *E. coli* W3110 transformed with pARH-III as described in Example 2, were assessed by immunoblotting using affinity-purified anti-angiogenin as described by Shapiro et al., 1988, supra. Cells displaying the highest level of expression (~10 mg/L) were selected for ARH-III expression.

Large-scale expression and purification were performed as described previously for angiogenin by Shapiro et al., 1988, supra. The hybrid ARH-III protein was thus expressed in *E. coli* W3110, refolded, and purified using Mono S cation exchange and C18 (octadecylsilane) reversed phase HPLC as described by Shapiro et al., 1988, supra. SEP-PAK C18 cartridges were from Millipore Corp. (Bedford, Mass. 01730). The ARH-III hybrid protein eluted earlier than angiogenin on the Mono S column (8 minute difference in retention time, 50 minute gradient from 0.15 to 0.55M NaCl in 10 mM Tris, pH 8.0). It eluted as a sharp, symmetrical peak on the C18 column with a small shoulder comprising 5% of the total area. The central fractions of the major peak were pooled and dialyzed, and SDS-PAGE analysis revealed a single compact band migrating at $M_r \sim 14,500$. The final yield was 0.4 mg/L culture.

The Met-(−1) residue of the *E. coli*-expressed ARH-III hybrid protein (9 μM) was removed enzymatically with Aeromonas aminopeptidase as described by Shapiro et al, 1988, supra, under conditions favorable for the spontaneous cyclization of the next residue, Gln-1, to pyroglutamic acid. The protein was then purified by reversed phase HPLC as above and peak fractions were pooled and dialyzed against water.

Although any native (non-mutated) or mutant (mutated) angiogenin expressed in *E. coli* using pAng2 contains Met-(−1) at the amino terminus, the extra residue has not yet been found to affect enzymatic or angiogenic activity. Nevertheless, because of its proximity to the replaced region in ARH-III, the N-terminal Met-(−1) residue was removed as described above to ensure that the binding and orientation of the new region would approximate that of angiogenin as closely as possible. Amino acid composition and peptide mapping indicate that removal of Met-(−1) in ARH-III was greater than 95% as described in Example 4 below.

EXAMPLE 4

Structural Characterization of ARH-III

Amino acid analysis was performed as described (Strydom et al., 1985, Biochemistry 24: 5486–5494) using a Picotag derivatization method and Waters Associates (Milford, Mass. 01757) HPLC system. Trypsin digestion was accomplished by incubating 4.1 nmol ARH-III with 95 pmol HPLC purified trypsin in 730 μL of 20 mM Tris, 0.35M NaCl, pH 8.0 for 24 hours at 37° C. The peptides were separated by reversed phase HPLC as described by Shapiro et al., 1988, supra, and identified by elution position and amino acid composition. An Altex ultrasphere IP C18 column was used with a linear gradient from 0–50% Solvent B (3:2:2, 2-propanol:acetonitrile:0.08% aqueous trifluoroacetic acid (TFA)) in Solvent A (0.1% TFA) over a period of 140 minutes. The flow rate of the column was 0.8 mL/minute.

SDS-PAGE was performed on 15% polyacrylamide gels with 5% stacking gels as described by Laemmli, 1970, Nature 227: 680–685. Proteins were visualized using rapid silver staining kit from ICN Immunobiologicals (Lisle, Ill. 60532).

Figure 4:
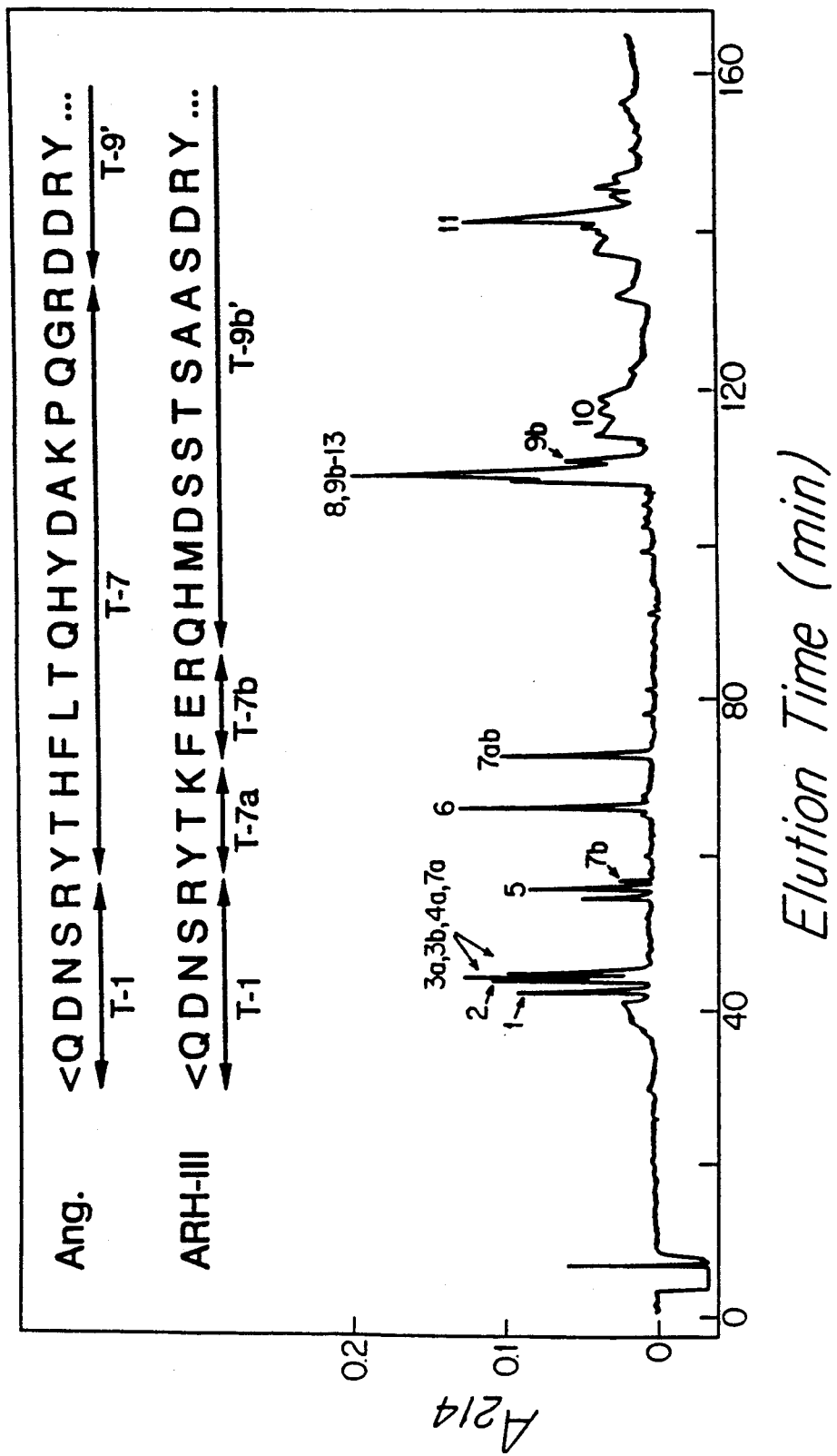
FIG. 4 shows an HPLC elution profile of tryptic peptides of ARH-III as described in Example 4.

The amino acid composition of ARH-III as shown in Table I was consistent with the successful replacement of residues 8–22 of angiogenin with residues 7–21 of RNase A, as well as the removal of Met-(−1). Results of a tryptic digest of ARH-III also supported the successful replacement of residues 8–22 as shown in Table I and FIG. 4. In particular, FIG. 4 shows an HPLC elution profile of tryptic peptides of ARH-III. Individual peptides identified by amino acid composition accounted for the entire sequence. Peptide designations for angiogenin are from Strydom et al., 1985, Biochemistry 24: 5486–5494. The N-terminal sequences of angiogenin and ARH-III are shown in FIG. 4; double-headed arrows indicate peptides generated by tryptic cleavage. All three cystine-linked peptide pairs, T-9b, T-10, and T-11, were recovered, consistent with the proper refolding and oxidation of the protein. Peptides T-1, -2, -3a, -3b, -4a, -5, -6, -8 and disulfide-linked T-10 and T-11 had compositions and elution positions essentially the same as those observed for human angiogenin (Strydom et al., 1985, supra; Shapiro et al., 1988, supra). The amino-terminal peptide T-1 was recovered in >95% yield, again indicating essentially complete removal of the Met-(−1).

As expected, the only differences between ARH-III and angiogenin occur with peptides T-7 and T-9'. In their places the ARH-III hybrid gives rise two new tripeptides (designated T-7a and T-7b) and an extended form of T-9' (designated T-9b') as shown in FIG. 4. T-7a eluted with three other peptides in two or more poorly resolved peaks at 44 and 45 minutes; they were identified by amino acid composition. Peptide T-7b (Table I) eluted as a discrete peak at 56 minutes as shown in FIG. 4. The unhydrolyzed hexapeptide constituting T-7ab was also recovered (FIG. 4; Table I). T-9b', which is disulfide-linked to T-9" to form the double peptide designated T-9b, was detected in two forms. First, the linked peptide T-9b eluted in essentially pure form in the peak at 111 minutes (FIG. 4, Table I). Second, the large peak at 109 minutes contains a mixture of T-8, T-9b, and 1 to 2 Arg residues. This is consistent with the incomplete cleavage of T-13 (an Arg-Arg dipeptide) from the carboxyl terminus of T-9b', and coelution of the T-9b'-13/T-9" double peptide with T-8.

TABLE I

Amino Acid Composition of ARH-III and Its Tryptic Peptides[a]

| | Angiogenin | ARH-III | T-7b | T-7ab | T-9b |
|---|---|---|---|---|---|
| Asp | 15 | 14.0 (14) | 0.14 | | 2.19 (2) |
| Glu | 10 | 9.9 (10) | 1.00 (1) | 0.98 (1) | 2.95 (3) |
| Ser | 9 | 12.6 (13) | 0.12 | | 6.56 (7) |
| Gly | 8 | 7.5 (7) | 0.12 | | 0.52 |
| His | 6 | 4.9 (5) | | | 1.11 (1) |
| Arg | 13 | 13.3 (13) | 1.00 (1) | 1.03 (1) | 2.17 (2) |
| Thr | 7 | 7.3 (7) | | 1.00 (1) | 2.87 (3) |
| Ala | 5 | 6.1 (6) | | | 1.87 (2) |
| Pro | 8 | 7.5 (7) | | | 0.18 |
| Tyr | 4 | 2.7 (3) | | 0.95 (1) | 0.86 (1) |
| Val | 5 | 4.0 (5) | | | 0.94 (1) |
| Met | 1 | 2.0 (2) | | | 1.81 (2) |
| Ile | 7 | 6.5 (7) | | | 1.03 (1) |
| Leu | 6 | 5.3 (5) | | 0.1 | 0.15 |
| Phe | 5 | 4.9 (5) | 0.90 (1) | 0.90 (1) | 0.98 (1) |
| Lys | 7 | 7.1 (7) | | 1.04 (1) | 1.23 (1) |
| Cys | 6 | 6 (6) | | | 2 (2) |
| pmol | | | 520 | 450 | 170 |

[a]Values are given as residues/mole; quantities less than 0.1 residue/mole are not shown. The numbers of residues predicted for the ARH-III sequence are shown in parentheses. Tryptic peptide compositions are from 200 μL aliquots of individual column fractions; pmol peptide per 200 μL are shown at the bottom. ARH-III Cys results are inferred from coelutions of disulfide linked peptides after tryptic digestion.

EXAMPLE 5

Enzymatic Assays and Activity

A. Enzymatic Assays

Activity toward yeast tRNA (obtained from Calbiochem) was determined using a precipitation assay (Shapiro et al., 1987, Proc. Natl. Acad. Sci. U.S.A. 84: 2238-2241) with angiogenin or ARH-III concentrations of 18-430 nM. FIG. 5a shows the activity of angiogenin and ARH-III measured toward the yeast tRNA. The assay measures the generation of acid-soluble fragments over 2 hours at pH 6.8° and 37° C. Assays for the pH profiles were performed using the f -(N-morpholino)ethanesulfonic acid (Mes), pH 5.4, 5.8, 6.3; N-(2-hydroxyethyl)piperazine-N'-2'-ethanesulfonic acid (Hepes) pH 6.2, 6.8, 7.3, 7.8; tris (hydroxymethyl)aminoethane (Tris), pH 7.5, 8.1, 8.5; and 2-(N-cyclohexylamino)ethanesulfonic acid (Ches), pH 8.8, 9.3, and 9.9. The pH values were calculated from the readings at 25° C. using $pk_a$/°C. values supplied by Research Organics (Cleveland, Ohio 44125). FIG. 5b shows the effects of pH on the activities of ARH-III (filled triangles), angiogenin (filled circles), and RNase (filled squares), toward yeast tRNA. For comparison, activities are normalized to the maximum $\Delta A_{260}$ obtained for each protein.

Activity toward dinucleotide (3',5') phosphates was determined by an HPLC quantitation method as described by Shapiro et al., 1988, Anal. Biochem. 175: 450-461; Harper and Vallee, 1989, Biochemistry 28: 1875-1884. Reaction mixtures (30 μL) contained 0.1 mM substrate, 2.8 μM ARH-III and were incubated for 4-24 hours at 37° C.

Ribonucleolytic activity toward 18S and 28S rRNA was visualized as described by Shapiro et al, 1986, Biochemistry 25: 3527-3532, with calf liver rRNA (Pharmacia) as substrate.

B. Enzymatic Activity

The enzymatic activities of ARH-III toward tRNA, 18S and 28S rRNA, and dinucleotide substrates were very similar to those of angiogenin. In the tRNA assay, both proteins exhibited a non-linear response for $\Delta A_{260}$ versus enzyme concentration at pH 6.8 (37° C.), and their activities were indistinguishable at the concentrations tested as shown in FIG. 5a. ARH-III did differ somewhat from angiogenin, however, in that its pH optimum was ~7.3 as shown in FIG. 5b. Angiogenin and RNase A (obtained from Cooper Biochemicals) had maximal activities under these assay conditions at pH ~6.8 and ~8.1, respectively, consistent with previous results obtained by Lee & Vallee, 1989b, Biochem. and Biophys. Res. Commun. 161: 121-126. It is known that angiogenin catalyzes the cleavage of dinucleotide substrates, but at rates 5-6 orders of magnitude lower than those observed for RNase A (Shapiro et al., 1988, Anal. Biochem. 175: 450-461; Harper & Vallee, 1989, Biochemistry 28: 1875-1884). Its specificity is different from that of RNase A based on $k_{cat}/K_m$ values for 4 different dinucleotides. The activity of ARH-III toward these substrates was very similar to that of angiogenin as shown in Table II. In all cases, $k_{cat}/K_m$ values were within 30% of those observed for angiogenin, and the relative specificity for the substrates was unchanged.

TABLE II

Activity of ARH-III toward Dinucleotide Substrates[a]

| | $k_{cat}/K_m$ (M$^{-1}$s$^{-1}$) | | |
|---|---|---|---|
| substrate | ARH-III | angiogenin[b] | RNase A[c] |
| CpA | 13 | 12 | $6.0 \times 10^6$ |
| CpG | 3.4 | 4.0 | $5.1 \times 10^5$ |
| UpA | 0.8 | 1.1 | $4.0 \times 10^6$ |
| UpG | 0.4 | 0.4 | $1.8 \times 10^5$ |

[a]Assays with ARH-III and angiogenin were performed in 30 mM Mes, 30 mM NaCl, pH 6.0 at 37° C.
[b]Values from Shapiro et al., 1988, Anal. Biochem. 175: 450-461 and Harper and Vallee, 1989, Biochemistry 28: 1875-1884.
[c]Values from Harper and Vallee, 1989. supra: assays performed spectrophotometrically in above buffer at 25° C.

It is also known that angiogenin cleaves naked 18S and 28S rRNA in a selective manner, yielding products of approximately 100-500 nucleotides in length which remain resistant to further degradation for some time (Shapiro et al., 1986, Biochemistry 25: 3527-3532). The activity of ARH-III toward such naked 18S and 28S rRNA was indistinguishable from that of angiogenin. In time points taken over 60-90 minutes, the two proteins (0.67 μM) catalyzed the formation of products of similar size and intensity, as revealed by agarose gel electrophoresis.

EXAMPLE 6

Inhibition of in vitro Protein Synthesis and Cleavage of Intact Ribosomes

The effect of ARH-III on protein translation in rabbit reticulocyte lysate was determined in a modification of the procedure of St. Clair et al., 1987, Proc. Natl. Acad. Sci. U.S.A. 84: 8330-8334, as described by Harper and Vallee, 1989, Biochemistry 28: 1875–1884. Reaction mixtures contained 10–210 nM angiogenin or ARH-III.

ARH-III catalyzed cleavage of reticulocyte ribosomal RNA in intact ribosomes was examined using the method of St. Clair et al., 1987, supra as described by Harper & Vallee, 1989, supra.

It is known that angiogenin inhibits translation in rabbit reticulocyte lysate by catalyzing a highly specific cleavage of 18S rRNA in the 40S ribosomal subunit, generating a small number of discrete products as observed by St. Clair et al., 1987, supra; St. Clair et al., 1988, Biochemistry 27: 7263–7268. RNase A, on the other hand, attacks the ribosome at numerous sites to form a huge number of reaction products of varying sizes. Of the two, angiogenin is actually more effective at inactivating the ribosomes, even though its rate with other RNA substrates is up to a million times slower than that of RNase A. This remarkable specificity is observed only with intact ribosomes or ribosomal subunits, but not with isolated 18S and 28S rRNA.

ARH-III was markedly less effective than angiogenin in inhibiting protein synthesis in rabbit reticulocyte lysate as shown in Table III. Whereas angiogenin inhibited protein translation completely at a concentration of 40–70 nM, ARH-III at 210 nM produced less than 50% inhibition, even with a 3-fold longer incubation time. A comparison of the amounts of protein required to generate similar levels of inhibition indicates that ARH-III was 20- to 30-fold less active than angiogenin in this assay system.

TABLE III

Inhibition of in vitro Protein Translation by ARH-III, Angiogenin and RNase A[a]

| Sample | Concentration (nM) | % Inhibition |
|---|---|---|
| ARH-III | 70 | 0 |
|  | 210 | 16 |
|  | 210[b] | 44 |
| Angiogenin | 10 | 15 |
|  | 30 | 86 |
|  | 70 | 100 |
| RNase A | 30 | 30 |
|  | 70 | 99 |

[a] Assays performed in rabbit reticulocyte lysate system. Percent inhibition based on amount of [$^{35}$S]-labeled protein recovered by acid precipitation; 0% and 100% inhibition correspond to 61,000 cpm and 200 cpm, respectively.
[b] Reaction time of ARH-III with lysate mixture was 45 minutes instead of the usual 15 minutes.

In order to determine whether ARH-III cleaves ribosomal RNA in the same selective manner as angiogenin, rRNA from the above rabbit reticulocyte lysate reaction mixtures was isolated, radiolabeled and analyzed by urea/polyacrylamide gel electrophoresis as shown in FIG. 6. Specifically, rabbit reticulocyte lysate was incubated for 15 minutes with H$_2$O (lanes 1 and 9), angiogenin at 10 nM (lane 2), 30 nM (lane 3) and 70 nM (lane 4), or ARH-III at 30 nM (lane 5), 70 nM (lane 6), 210 nM (lane 7), and 210 nM with a 45 minute incubation (lane 8). The rRNA was then purified by phenol/chloroform extraction and ethanol precipitation, 5' labeled using [$\gamma$-$^{32}$P]-ATP, electrophoresed on a polyacrylamide gel, and visualized by autoradiography. Samples in lanes 1–4 of FIG. 6 were loaded and electrophoresed for 5 minutes before loading lanes 5–9. ARH-III generated essentially the same pattern of cleavage products as angiogenin, but required much higher concentrations to do so. Thus, it took a 45 minute incubation time for 210 nM ARH-III to yield products with the same intensity as those generated by 20 nM angiogenin with a 15 minute incubation time. This is consistent with a 30-fold difference in activity.

EXAMPLE 7

Biological Activity

Angiogenesis was assessed using the chick embryo CAM assay of Knighton et al., 1977, Br. J. Cancer 35: 347–356, as described by Fett et al., 1985, Biochemistry 24: 5480–5486. Individual assays employed sets of 10–20 eggs. The total number of eggs used was 248 for ARH-III, 125 for angiogenin, and 20 for H$_2$O. Angiogenin was from the E. coli expression system described in Example 3 and contained a Met-(1) residue; its potency was indistinguishable from that of native angiogenin containing pyroglutamic acid at the amino terminus (Shapiro et al., 1988, Anal. Biochem. 175: 450–461). The dose response of ARH-III in the CAM assay was different from that of angiogenin as shown in FIG. 7. Angiogenin typically approaches maximal activity at a dose of approximately 1 ng, inducing a positive response in 50–60% of the eggs. Its activity at 0.1 ng is usually close to the 15–20% positive background level observed with water alone. In contrast, ARH-III reached full activity at 0.1 ng, and in this respect was 10-fold more potent than angiogenin. This was unexpected since RNase itself has no angiogenic activity and the ARH-III hybrid contains an RNase-derived segment in what is considered to be a region unique to angiogenic structure and function. At higher doses, ARH-III elicited a maximal response of 41% positive, which was slightly less than that of angiogenin.

EXAMPLE 8

Binding of ARH-III to PRI

The apparent second-order association constant, $k_a$, for the binding of ARH-III to PRI was determined by examining the competition between ARH-III and RNase A for PRI, as described by Lee & Vallee, 1989a, Biochemistry 28: 3556–3561 and Lee et al., 1989a, Biochemistry 28: 219–224. PRI was purified as described by Blackburn, 1979, J. Biol. Chem. 254: 12484–12487. The interaction was monitored in 0.1M Mes, 0.1M NaCl, 1 mM EDTA, pH 6.0 at 25° C. The $k_a$ value obtained for ARH-III was the average of seven separate determinations. The $k_a$ determined for the association of ARH-III and PRI was $(4.3 \pm 0.5) \times 10^8$ M$^{-1}$s$^{-1}$. This value was more than twice that for angiogenin as shown in Table IV.

Figure 8:
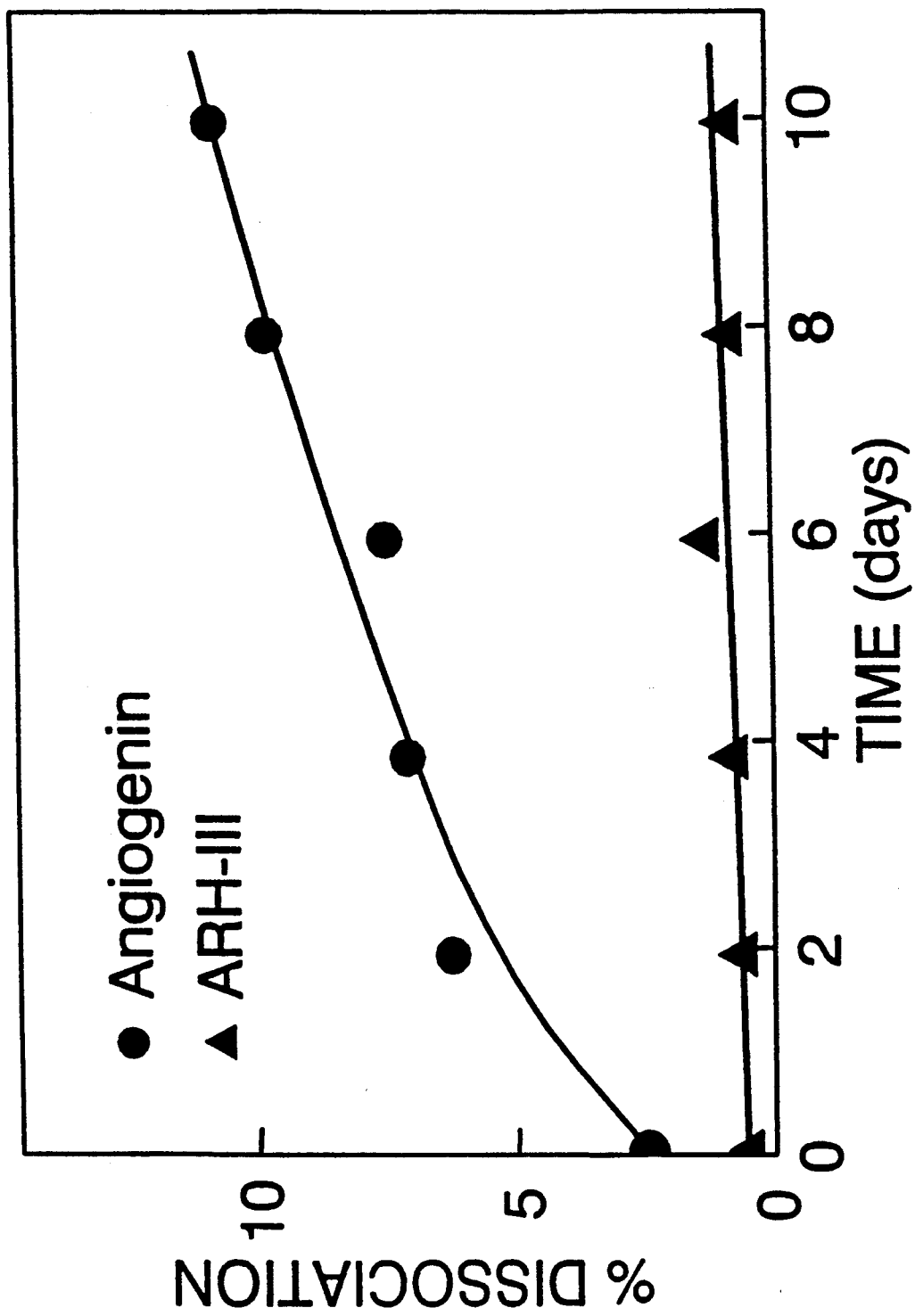
FIG. 8 a graph showing the dissociation of angiogenin and ARH-III from protein:PRI complex over 10 days.

The dissociation rate constant, $k_d$, was determined by monitoring the release of ARH-III from the protein:inhibitor complex as a function of time in the presence of excess scavenger for free PRI as described by Lee & Vallee, 1989a, supra, and Lee et al., 1989b, Biochemistry 28: 225–230. Free angiogenin and ARH-III were measured by cation-exchange HPLC over a 10 day period. The incubation was performed at 25° C. in the above buffer containing 120 $\mu$M DTT. The dissociation rate for the ARH-III:PRI complex was substantially slower than that for angiogenin as shown in Table IV. FIG. 8 also shows the dissociation of angiogenin and ARH-III from the protein:PRI complex over 10 days. The y-axis of FIG. 8 depicts the fraction of angiogenin or ARH-III which is unbound. Over the 10 day period, during which ~8% of the angiogenin:PRI complex dissociated, there was no detectable (<2%) dissociation of the ARH-III:PRI complex. Thus, the upper limit for the $k_d$ for ARH-III can be set conservatively at $3 \times 10^{-8}$ s$^{-1}$.

The $K_i$ for the interaction of ARH-III and PRI, calculated from the $k_a$ and $k_d$ values was $\leq 7 \times 10^{-17}$M. This was at least 10- and 600-fold lower than the values for angiogenin and RNase A, respectively.

TABLE IV

Binding Constants for ARH-III with PRI[a]

| Sample | $k_a$ (M$^{-1}$s$^{-1}$ × 10$^{-8}$) | $k^d$ (s$^{-1}$ × 10$^7$) | $K_i$ (fM) |
|---|---|---|---|
| ARH-III | 4.3 | ≤0.3 | ≤0.07 |
| Angiogenin[b] | 1.8 | 1.3 | 0.7 |
| RNase A[b] | 3.4 | 150 | 40 |

[a]Incubation conditions were 0.1 M Mes, 0.1 M NaCl, 1 mM EDTA, pH 6.0., 25° C.
[b]From Lee et al., 1989b, Biochemistry 28: 225-230.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A covalent hybrid mutant angiogenin protein comprising an N-terminal sequence wherein amino acids in a region at or corresponding to human angiogenin residues 8-22 have been replaced with a sequence of amino acids that is identical to or conservatively substituted from the sequence corresponding to mammalian RNase residues 7-21, and wherein the covalent hybrid mutant angiogenin protein has increased angiogenic activity as compared with angiogenin.

2. A covalent hybrid mutant angiogenin protein according to claim 1 wherein the amino acids in the region at or corresponding to human angiogenin residues 8-22 are the amino acid residues 8-22 shown for angiogenin in FIG. 2a.

3. A covalent hybrid mutant angiogenin protein according to claim 2 wherein the amino acids corresponding to mammalian RNase residues 7-21 are the amino acid residues 7-21 shown for RNase A in FIG. 2a.

4. A covalent hybrid mutant angiogenin protein according to claim 1 that is ARH-III.

5. A pharmaceutical composition comprising an angiogenic effective amount of the protein of claim 1 in a pharmaceutically acceptable carrier.

6. A pharmaceutical composition comprising an angiogenic effective amount of the protein of claim 2 in a pharmaceutically acceptable carrier.

7. A pharmaceutical composition comprising an angiogenic effective amount of the protein of claim 3 in a pharmaceutically acceptable carrier.

8. A pharmaceutical composition comprising an angiogenic effective amount of the protein of claim 4 in a pharmaceutically acceptable carrier.

* * * * *